US005835216A

United States Patent [19]
Koskinen

[11] Patent Number: 5,835,216
[45] Date of Patent: *Nov. 10, 1998

[54] METHOD OF CONTROLLING A SHORT-ETALON FABRY-PEROT INTERFEROMETER USED IN AN NDIR MEARSUREMENT APPARATUS

[75] Inventor: Yrjö Koskinen, Helsinki, Finland

[73] Assignee: Vaisala Oy, Helsinki, Finland

[*] Notice: This patent issued on a continued prosecution application filed under 37 CFR 1.53(d), and is subject to the twenty year patent term provisions of 35 U.S.C. 154(a)(2).

[21] Appl. No.: 675,858

[22] Filed: Jul. 5, 1996

[30] Foreign Application Priority Data

Jul. 7, 1995 [FI] Finland ..................... 953370

[51] Int. Cl.[6] .................................. G01B 9/02
[52] U.S. Cl. ........................... 356/352; 356/346
[58] Field of Search .................... 356/345, 346, 356/352

[56] References Cited

U.S. PATENT DOCUMENTS 3,914,055  10/1975  Wolga et al. .
5,218,422   6/1993  Zoechbauer ........................ 356/352
5,561,523  10/1996  Blomberg et al. .................. 356/352

FOREIGN PATENT DOCUMENTS 0 608 049 A2  7/1994  European Pat. Off. .
WO91 05988    5/1991  WIPO .

Primary Examiner—Robert Kim

[57] ABSTRACT

A method of controlling a short-etalon Fabry-Perot interferometer used in an NDIR measurement apparatus includes generating a measurement signal using a radiant source. The measurement signal is provided to a sample point containing a gas mixture to be measured. The measurement signal is bandpass-filtered with an electrically tuneable Fabry-Perot interferometer using at least two wavelengths of the interferometer passband. The measurement signal is passed via an optical filter component prior to detection, and the filtered measurement signal is detected by a detector. During the measurement cycle, the passband frequency of the interferometer is controlled to coincide at least partially with the cutoff wavelength range of the optical filter component.

20 Claims, 2 Drawing Sheets

METHOD OF CONTROLLING A SHORT-ETALON FABRY-PEROT INTERFEROMETER USED IN AN NDIR MEARSUREMENT APPARATUS

BACKGROUND OF THE INVENTION

1. Field of the Invention

The present invention is related to a method according to the preamble of claim 1 for controlling a short-etalon Fabry-Perot interferometer used in an NDIR measurement apparatus.

2. Description of the Background Art

Nondispersive infrared measurement equipment are conventionally used for gas concentration measurements. The method can be made extremely selective with respect to the gas to be measured by limiting the wavelength range used for the measurement to coincide with the characteristic absorption band of the gas under measurement. In the NDIR method, the wavelength range is generally selected by means of a bandpass filter. Disclosed in the EP patent application 94300082.8 is a tuneable interferometer suited for replacing an optical bandpass filter of an NDIR measurement apparatus. The passband wavelength of the interferometer is voltage-controlled thus making the interferometer capable of sweeping measurements in which the measurement can be made at two or a greater number of wavelengths. Here, it is advantageous to measure the gas to be analyzed exactly at its absorption band while the reference measurement is made at an adjacent wavelength. Thus, the reference measurement facilitates compensation of aging processes and temperature dependence in the measurement equipment. Further, it is possible to determine the concentrations of a plurality of different gases by making the measurements at wavelengths corresponding to the absorption bands of said gases.

When using such a tuneable interferometer, it is crucial to the stability of the measurement how well the voltage dependence of the center wavelength of the interferometer passband stays constant. In cited EP patent application 94300082.8 is further disclosed a tuneable short-etalon interferometer intended for gas concentration measurements. The passband wavelength of the interferometer is adjusted by altering the distance between the interferometer mirrors with the help of an electrostatical force. Such an interferometer can be manufactured by surface micromechanical techniques so as to comprise a plurality of superimposed, IR radiation transmitting thin-film layers, whose thickness is selected to make the multilayer structures perform as the mirrors of the interferometer.

Conventionally, the IR radiation used in the NDIR measurement equipment is modulated. The purpose of this arrangement is to obtain an AC signal out from the detector which is advantageous in terms of noise and drift compensation in the electronic circuitry. The IR radiation can be modulated by chopping the input power to the IR radiation source. For this, however, a sufficiently short thermal time constant is assumed from the IR radiation source to facilitate a sufficiently high modulation rate. A suitable IR radiation source is formed by, e.g., a microlamp permitting a modulation rate as high as about 10 Hz. However, the modulation of the glow filament temperature causes an extra stress which shortens the service life of the lamp filament. To achieve a higher radiation output power, a heatable element of larger radiating area must be used, whereby the heating rate is retarded. Thence, the radiation has to be modulated with the help of a separate mechanical chopper placed on the optical path of the radiation. Unfortunately, the service life of such a mechanical chopper is limited.

In the long run, the internal stress of the interferometer mirror may drift causing a change in the curvature of the mirror. This in turn shifts the mutual distance of the mirrors at a given level of the control voltage thus also shifting the passband wavelength of the interferometer. Resultingly, instability occurs in the function of the NDIR measurement apparatus.

SUMMARY OF THE INVENTION

It is an object of the present invention to overcome the drawbacks of the above-described techniques and to achieve an entirely novel type of method for controlling a short-etalon Fabry-Perot interferometer used in an NDIR measurement apparatus.

A goal of the invention is achieved by adjusting the passband wavelength of said short-etalon Fabry-Perot interferometer to coincide at least partially with the cutoff wavelength range of the optical filter in said NDIR measurement apparatus. According to a preferred embodiment of the invention, the entire passband of the interferometer is controlled in a cyclically repetitive manner sufficiently far into the cutoff wavelength range of the optical filter in order to use the interferometer as an amplitude modulator of the IR radiation. According to another preferred embodiment of the invention, the voltage dependence curve of the interferometer length is calibrated by controlling the interferometer passband to coincide with the optical filter cutoff edge wavelength, whereby such a stable passband wavelength gives a fixed reference point for the voltage dependence curve of the interferometer.

The invention offers significant benefits.

The method according to the invention for controlling the interferometer replaces the use of a mechanical chopper or electrical modulation of the IR radiation source.

Hence, an embodiment according to the invention provides both a lower cost and longer service life. According to the invention, the IR radiation source can be driven by a DC source, which is more cost-efficient and imposes no additional stress on the IR radiation source due to its temperature modulation.

Furthermore, the automatic calibration method according to the invention gives the NDIR measurement equipment a good long-term stability and removes the need for a separate calibration step.

BRIEF DESCRIPTION OF THE DRAWINGS

In the following the invention is described in greater detail with reference to embodiments of the invention illustrated in the appended diagrams in which.

DETAILED DESCRIPTION OF THE PREFERRED EMBODIMENTS

Figure 1:
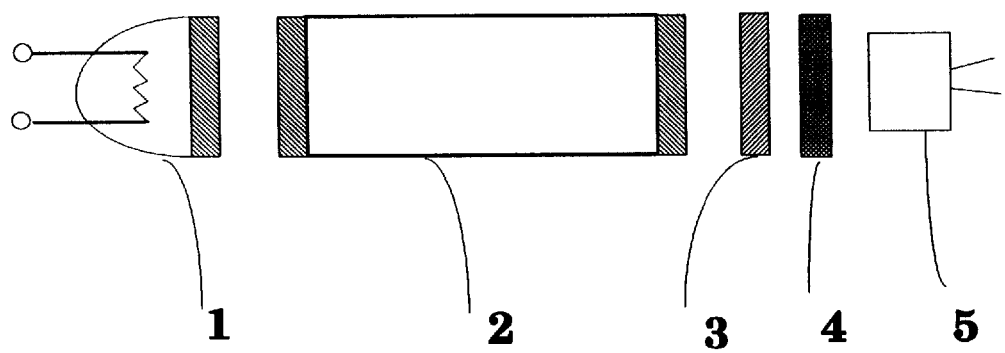
FIG. 1 is a schematic longitudinally sectioned side view of an NDIR apparatus suited to implement the invention.

Referring to FIG. 1, an NDIR measurement apparatus utilizing a short-etalon interferometer is outlined. The measurement apparatus comprises the following components:

a radiation source 1, a measurement channel 2, an optical longpass filter 3, a voltage-tuneable short-etalon interferometer 4, and a detector 5.

The radiation source 1 is formed by a wideband thermal IR radiation source such as an incandescent lamp, for example. The radiation emitted by the source is passed into the measurement channel 2 containing the gas under measurement. The amount of radiation passed through the measurement channel is detected by means of the detector 5. Prior to detection, a wavelength range useful for the measurement is selected from the wideband spectrum of radiation by means of the optical longpass filter 3 and the interferometer 4. The interferometer 4 is utilized so that the measurement is performed by virtue of the voltage control at two passband wavelengths corresponding to: the absorption band wavelength and the reference wavelength. The absorption band wavelength is selected to coincide with the characteristic absorption spectrum of the gas under measurement so that concentration-dependent absorption caused by the gas under measurement causes a decrease in the amplitude of the signal obtained from the detector output. The reference wavelength is selected adjacent to the absorption band wavelength. The purpose of the measurement at this wavelength is to provide a signal independent from the concentration of the gas under measurement that represents the basic intensity of radiation passing the measurement channel without absorption and that can be used for the error compensation of changes in the intensity of radiation transmitted from the source.

Figure 2:
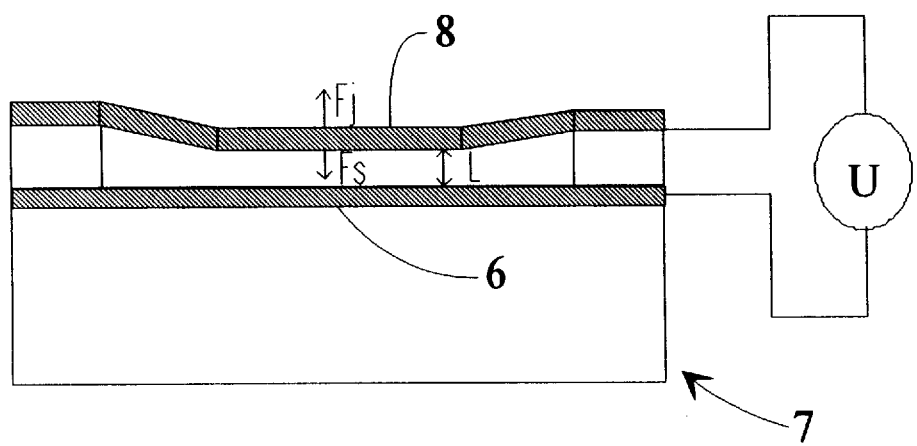
FIG. 2 is a schematic longitudinally sectioned side view of a short-etalon Fabry-Perot interferometer suited for control according to the invention.

Referring to FIG. 2, shown therein is a schematic diagram of an electrostatically tuneable short-etalon interferometer having the lower mirror 6 forming the stationary part of the interferometer 7 and the upper mirror 8 acting as the part which is movable by means of a control voltage U. The interferometer 7 may be fabricated by surface micromechanical techniques, whereby the upper mirror 8 is formed by a flexible multilayer thin-film structure. The distance L between the mirrors of the IR-band short-etalon interferometer is typically in the range 0.5–5 $\mu$m.

The distance L between the mirrors 6 and 8 is controlled by means of an external voltage U. The force of electrostatic attraction between the mirrors is obtained from the formula $$F_s = \epsilon A/2 (U/L)^2 \quad (1)$$

where $\epsilon$ is the dielectric constant of a vacuum and A is the surface area of the mirror. The force opposing the movement of the upper mirror 8 can be described with sufficient accuracy by a single spring constant k. Denoting the distance between the mirrors at rest by $L_0$, the spring force $F_j$ may be written $$F_j = k (L_0 - L) \quad (2)$$

The change in the distance between the mirrors 6 and 8 caused by a given control voltage can be written assuming that in a static situation the electrostatic force and the spring force are equal in magnitude ($F_s = F_j$) but acting in opposite directions $$\epsilon A/2 (U/L)^2 = k (L_0 - L) \quad (3)$$

Figure 3:
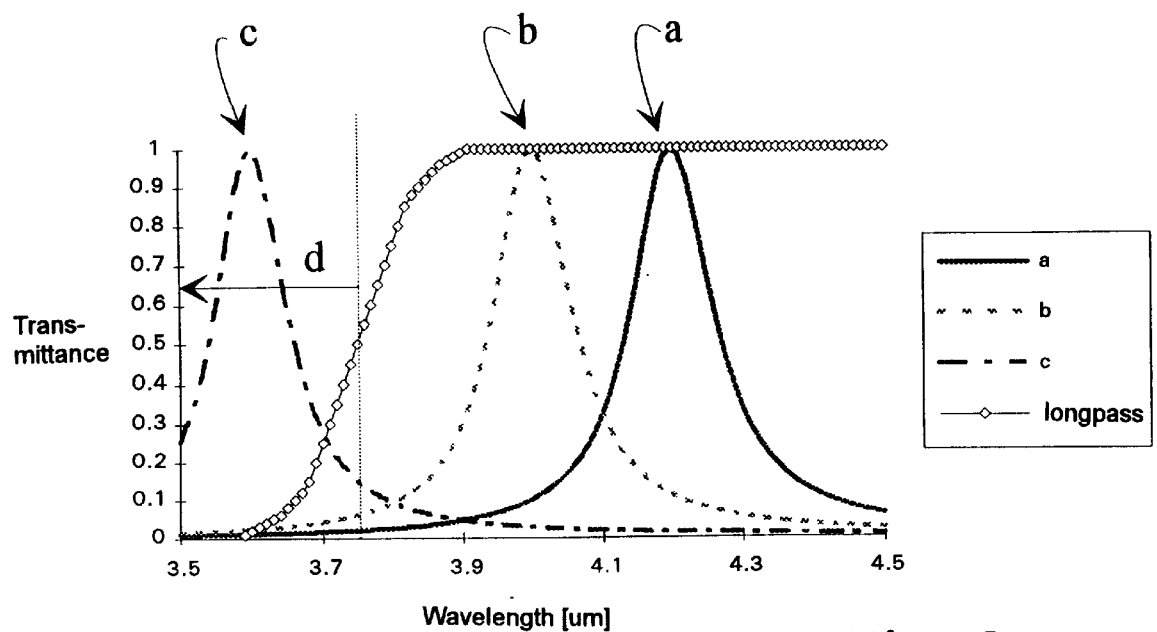
FIG. 3 is a graph showing the passband curves of the interferometer controlled according to the invention plotted at different instants of the modulation cycle.

In FIG. 3 are shown the relationship between the absorption band a and the reference wavelength band b when the distance between the mirrors of the short-etalon interferometer is controlled to 2.1 $\mu$m and 2.0 $\mu$m, respectively. The distance between the mirrors 6 and 8 is selected for measurements of carbon dioxide concentration. The absorption spectrum of carbon dioxide is centered at 4.26 $\mu$m wavelength.

Conventionally, the radiation passed in an NDIR measurement apparatus through the measurement channel is amplitude-modulated either by electrically chopping the input power to the radiation source or mechanically using a separate optical chopper. Then, the detector output provides an AC signal from which the offset component of the detector dark signal is eliminated. The AC signal is also useful in drift compensation of the detector signal amplifier circuit. Furthermore, the noise component of the signal can be reduced by passing the signal through a narrowband filter. When using a pyroelectric detector, the radiation must necessarily be modulated, because a pyroelectric detector is sensitive to intensity changes of the radiation alone and does not give any DC output signal as a response to a constant level of impinging radiation.

In the embodiment according to the invention, the amplitude-modulation of radiation intensity is implemented, e.g., by means of the interferometer 7 shown in FIG. 2. Modulation is achieved as shown in FIG. 3 by setting the control voltage of the interferometer 7 so that the interferometer passband is shifted outside the passband of the optical longpass filter, into its cutoff wavelength range d. Thus, the use of the "blanked" passband c obtained as shown in FIG. 3 by controlling the interferometer passband wavelength sufficiently far to the optical longpass filter cutoff wavelength range d replaces the conventional method of chopping the radiation source. The detector provides an AC signal when the interferometer passband wavelength is alternated between the "blanked" passband and the active passbands a and b.

The "blanked" passband shown in FIG. 3 is achieved by controlling the distance between the interferometer mirrors to 1.9 $\mu$m. The distance between the mirrors of a voltage-tuneable interferometer can be brought down to approx. 25% of the distance between the mirrors in an interferometer at rest. Hence, the different passbands shown in FIG. 3 are clearly within the wavelength sweep range of a single interferometer structure.

The "blanked" passband can basically be used in two different ways for the control of the interferometer:

1. The interferometer passband wavelength is cyclically shifted between wavelengths of the blanked passband c and the absorption passband a of the gas under measurement. Then, the detector provides an AC output signal whose amplitude is proportional to the intensity of radiation impinging on the detector within the wavelength range of the absorption passband. Correspondingly, the reference output signal is obtained by shifting the wavelength of the interferometer passband between the blanked passband c and the reference passband b.

2. The interferometer passband wavelength is cyclically shifted in a sequence between the wavelengths of the passbands a, b and c and the corresponding output signals $S_a$, $S_b$ and $S_c$, of the detector are recorded synchronized with the wavelength shifts of the interferometer passband, respectively. The output signal values are stored in the memory of a microprocessor used for controlling the measurement apparatus, after which the value $S_c$, of the detector "blanked" output signal is deducted from the signal values $S_a$ and $S_b$. To improve the signal-to-noise ratio, the measurement sequence can be repeated cyclically several times for averaging the measurement results.

For stable operation of the interferometer 7, it is important that the wavelength of interferometer passband at a given value of the control voltage stays maximally constant. A change in the spring constant of the upper mirror 8 causes a change in the distance between the interferometer mirrors resulting in a corresponding drift of the passband wavelength. Such a drift may be caused by, e.g., a change in the internal stresses of the upper mirror 8. The calibration method according to the invention utilizes an integral wavelength reference by virtue of which the effect of the change in the spring constant of the mirror at the wavelength of interferometer passband can be eliminated by computing a suitable factor of correction to be used in the drift correction of the interferometer control voltage.

The calibration method is based on utilizing on the path of the measurement channel an IR radiation transmitting element with such a suitable shape of the transmittance curve that has a cutoff edge, a transmittance minimum or a transmittance maximum capable of performing as a wavelength reference. Thence, the method can employ an optical longpass filter such as the one illustrated in FIG. 3 with the passband cutoff edge wavelength tuned at approx. 3.8 $\mu$m.

Figure 4:
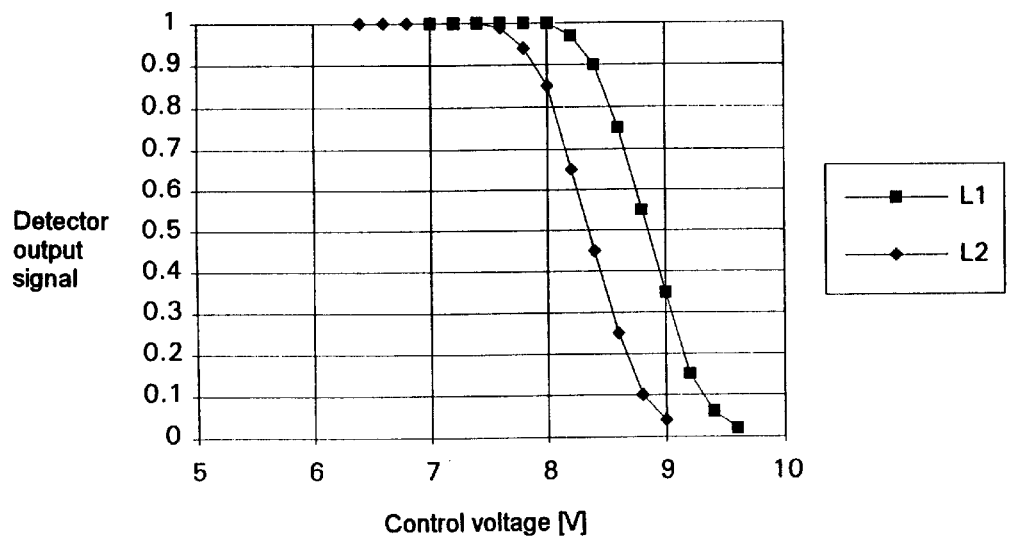
FIG. 4 is a graph with the detector output signal amplitudes plotted vs. the different values of the interferometer control voltage when the optical path is provided with the optical longpass filter of FIG. 3.

Referring to FIG. 4, the detector output signal amplitude is plotted therein for different values of the interferometer control voltage when the optical path is provided with a longpass filter 3 illustrated in FIG. 3. As is evident from the diagram, when the control voltage is increased, the amplitude of the detector output signal obtained from the interferometer channel starts to drop by the cutoff effect of the optical longpass filter 3. The interferometer passband control curves L1 and L2 shown in FIG. 4 differ from each other due to a change in the spring constant of the upper mirror 8. In more detail, owing to a change in the spring constant of the upper mirror 8, the passband control curve L1 has the passband control voltage of the interferometer 4 corresponding to the cutoff edge wavelength of the optical longpass filter 3 shifted by approx. 0.4 V in comparison with curve L2. Obviously, the distance L between the interferometer mirrors 6 and 8 is equal on both curves L1 and L2 for equal transmittance percentage values of, e.g., 50%, corresponding to a control voltage of 8.4 V on curve L1 and 8.8 V on curve L2.

The automatic calibration method based on utilizing an optical longpass filter 3 as a wavelength reference can be applied in, e.g., the following way:

the reference wavelength is defined to be, on the cutoff edge of the optical longpass filter transmittance curve, that wavelength at which the detector output signal is reduced to 50% from its maximum value, the factory calibration is made so that the interferometer control voltage is swept over a suitable voltage span with the help of a microprocessor, the measurement values are stored in the memory of the microcomputer and the control voltage value $U_a$ corresponding to said 50% reduction in detector output signal amplitude is computed by, e.g., interpolation, the thus obtained value $U_a$ is stored in the memory of the microcomputer, the automatic calibration cycle of the measurement apparatus is performed analogously to factory calibration in order to identify a possible change in the transmittance properties of the apparatus and the new value $U_b$ corresponding to said 50% reduction in detector output signal amplitude is computed, the gas concentration measurements are subsequently performed using a control voltage value corrected by the factor $U_b/U_a$ as the interferometer control voltage. Hence, for example, if the absorption band of carbon dioxide during factory calibration was coincident with a value $UC_{CO2}$ of the interferometer control voltage, a corrected value $(U_b/U_a) * U_{CO2}$ of the control voltage will be used during measurements.

The longpass filter 3 is selected so that no absorption spectrum components of other gases possibly disturbing the measurement can occur at the wavelength of the cutoff edge of the filter spectral transmittance curve. With the help of the microprocessor incorporated in the measurement apparatus, the wavelength reference obtained from the cutoff edge wavelength of the optical longpass filter may also be resolved using more advanced curve-fitting computational algorithms. Hence, the above-described technique using the 50% reduced signal value must be understood as an exemplifying method only.

On the basis of Equation 3 above, it can be shown that the same correction factor $U_b/U_a$ may be universally used for all values of the interferometer control voltage. A precondition to this is, however, that the model of a single spring constant can describe the motion of the upper mirror 8 with a sufficient accuracy.

The longpass filter 3 typically is an interference filter manufactured as a multilayer thin-film structure. A disadvantage in the use of an interference filter for an automatic calibration process is related to the temperature dependence of the filter spectral transmission curve. In this respect, a better alternative is to use, e.g., a suitable glass grade having a transmittance minimum within the wavelength sweep range of the interferometer. For example, the spectral transmittance curve of a thin Vycor glass plate is suitable for carbon dioxide gas concentration measurement, since this glass grade has a distinct transmittance minimum at approx. 4 $\mu$m. Analogously to the edge wavelength of a longpass filter, such a transmittance minimum can be utilized as a wavelength reference in the calibration of an interferometer. Here, the measurement results of the spectral sweep obtained by means of the interferometer must be corrected according to the spectral transmittance curve of the glass. Alternatively, a suitable type of radiation-transmitting polymer may be used as the wavelength reference.

I claim:

1. A method of controlling a short-etalon Fabry-Perot interferometer used in a nondispersive infrared measurement apparatus, comprising the steps of:

a) generating a radiant measurement signal;

b) directing the radiant measurement signal into a sample of a gas mixture to be measured to provide a sample measurement signal;

c) optically filtering the sample measurement signal;

d) bandpass-filtering the optically filtered measurement signal using at least first and second wavelengths of a passband of an electrically tuneable Fabry-Perot interferometer; and e) detecting the bandpass-filtered measurement signal, during a measurement cycle, the passband wavelength of the interferometer being controlled in said step d) to alternate cyclically between a cutoff wavelength and the first wavelength and then between the cutoff wavelength and the second wavelength, the cutoff wavelength of the interferometer at least partially coinciding with a cutoff wavelength range of said step c) of optically filtering in which the sample measurement signal does not pass.

2. The method as defined in claim 1, wherein said step c) comprises optically filtering the sample measurement signal with an optical component having a spectral transmittance curve with a transmittance minimum or cutoff edge within a wavelength sweep range of the interferometer, the transmittance minimum or cutoff edge being used as a wavelength reference for control voltage calibration of the interferometer.

3. The method as defined in claim 2, wherein the optical component is IR radiation transmitting glass or a polymer.

4. The method as defined in claim 1, wherein said step c) comprises optically filtering the sample measurement signal with an optical longpass filter.

5. The method as defined in claim 4, wherein the optical longpass filter is IR radiation transmitting glass or a polymer.

6. The method as defined in claim 1, wherein said step c) comprises optically filtering the sample measurement signal with IR radiation transmitting glass or a polymer.

7. A nondispersive infrared measurement method comprising the steps of:

a) generating infrared measurement light;

b) directing the infrared measurement light into a gas sample to provide sample measurement light;

c) optically filtering the sample measurement light to provide filtered measurement light which is cut-off below a predetermined cut-off wavelength;

d) amplitude modulating the filtered measurement light with an interferometer having a passband that alternates between a blanked passband below the predetermined cut-off wavelength and first and second active passbands greater than the predetermined cut-off wavelength which respectively correspond to an absorption band of the gas sample and a reference passband, the filtered measurement light not being passed by the interferometer when the passband of the interferometer is the blanked passband; and e) optically detecting the amplitude modulated measurement light to provide a measurement signal indicative of a concentration of the gas sample, said step d) comprising controlling the passband of the interferometer to alternate cyclically between the blanked passband and the first active passband and then between the blanked passband and the second active passband.

8. The non-dispersive infrared measurement method of claim 7, wherein said step c) comprises optically filtering the sample measurement light with an optical component having a spectral transmittance curve with a transmittance minimum or cut-off edge within a wavelength sweep range of the interferometer, the transmittance minimum or cut-off edge being used as a wavelength reference for control voltage calibration of the interferometer.

9. The non-dispersive infrared measurement method of claim 8, wherein the optical component is a longpass filter.

10. The non-dispersive infrared measurement method of claim 8, wherein the optical component is infrared radiation transmitting glass.

11. The non-dispersive infrared measurement method of claim 8, wherein the optical component is a polymer.

12. The non-dispersive infrared measurement method of claim 7, wherein the interferometer is a Fabry-Perot interferometer.

13. A method of controlling a short-etalon Fabry-Perot interferometer used in a nondispersive infrared measurement apparatus, comprising the steps of:

a) generating a radiant measurement signal;

b) directing the radiant measurement signal into a sample of a gas mixture to be measured to provide a sample measurement signal;

c) optically filtering the sample measurement signal;

d) bandpass-filtering the optically filtered measurement signal using at least two wavelengths of a passband of an electrically tuneable Fabry-Perot interferometer; and e) detecting the bandpass-filtered measurement signal, during a measurement cycle, the passband wavelength of the interferometer being controlled to coincide at least partially with a cutoff wavelength range of said step c) of optically filtering, said step c) comprising optically filtering the sample measurement signal with an optical component having a spectral transmittance curve with a transmittance minimum or cutoff edge within a wavelength sweep range of the interferometer, the transmittance minimum or cutoff edge being used as a wavelength reference for control voltage calibration of the interferometer.

14. The method as defined in claim 13, wherein the passband of the interferometer is controlled in a cyclically repetitive sequence to coincide with a cutoff wavelength range of said step c) of optically filtering for amplitude-modulating the optically filtered measurement signal.

15. The method as defined in claim 14, wherein said step c) comprises optically filtering the sample measurement signal with an optical longpass filter.

16. The method as defined in claim 14, wherein said step c) comprises optically filtering the sample measurement signal with IR radiation transmitting glass or a polymer.

17. The method as defined in claim 13, wherein the optical component is an optical longpass filter.

18. A nondispersive infrared measurement method comprising the steps of:

a) generating infrared measurement light;

b) directing the infrared measurement light into a gas sample to provide sample measurement light;

c) optically filtering the sample measurement light to provide filtered measurement light which is cut-off below a predetermined cut-off wavelength;

d) amplitude modulating the filtered measurement light with an interferometer having a passband that alternates between a blanked passband below the predetermined cut-off wavelength and first and second active passbands greater than the predetermined cut-off wavelength which respectively correspond to an absorption band of the gas sample and a reference passband; and e) optically detecting the amplitude modulated measurement light to provide a measurement signal indicative of a concentration of the gas sample, said step c) comprising optically filtering the sample measurement light with an optical component having a spectral transmittance curve with a transmittance minimum or cut-off edge within a wavelength sweep range of the interferometer, the transmittance minimum or cut-off edge being used as a wavelength reference for control voltage calibration of the interferometer.

19. The nondispersive infrared measurement method of claim 18, wherein the passband of the interferometer in said step d) is alternated cyclically between the blanked passband and the first active passband and then between the blanked passband and the second active passband.

20. The nondispersive infrared measurement method of claim 18, wherein the passband of the interferometer in said step d) is alternated cyclically in sequence between the blanked passband, the first active passband and the second active passband.

* * * * *